United States Patent
Jacquin et al.

(10) Patent No.: US 10,766,846 B2
(45) Date of Patent: Sep. 8, 2020

(54) METHOD FOR PRODUCING AND PURIFYING 1,3-BUTADIENE

(71) Applicants: IFP Energies Nouvelles, Rueil-Malmaison (FR); Compagnie Generale des Etablissements Michelin, Clermont-Ferrand (FR)

(72) Inventors: Marc Jacquin, Lyons (FR); Nuno Pacheco, Clermont-Ferrand (FR); Rejane Dastillung, Lyons (FR); Sophie Couderc, Neuilly sur Seine (FR); Claire Fauvarque Nuytien, Clermont-Ferrand (FR)

(73) Assignees: IFP Energies Nouvelles, Rueil-Malmaison (FR); Compagnie Generale des Etablissements Michelin, Clermont-Ferrand (FR)

( * ) Notice: Subject to any disclaimer, the term of this patent is extended or adjusted under 35 U.S.C. 154(b) by 0 days.

(21) Appl. No.: 16/341,500

(22) PCT Filed: Oct. 12, 2017

(86) PCT No.: PCT/EP2017/076057
§ 371 (c)(1),
(2) Date: Apr. 12, 2019

(87) PCT Pub. No.: WO2018/069441
PCT Pub. Date: Apr. 19, 2018

(65) Prior Publication Data
US 2019/0300470 A1    Oct. 3, 2019

(30) Foreign Application Priority Data
Oct. 14, 2016   (FR) ..................... 16 59995

(51) Int. Cl.
*C07C 67/08*   (2006.01)
*C07C 1/213*   (2006.01)
(Continued)

(52) U.S. Cl.
CPC .............. *C07C 67/08* (2013.01); *C07C 1/213* (2013.01); *C07C 7/005* (2013.01); *C07C 7/06* (2013.01)

(58) Field of Classification Search
CPC ... C07C 1/20–213; C07C 69/16; C07C 67/08; C07C 11/167; C07C 1/213; C07C 7/005; C07C 7/06
See application file for complete search history.

(56) References Cited

U.S. PATENT DOCUMENTS 2,372,221 A * 3/1945 Morell ................ C07C 67/08
                                                  560/263
2,383,205 A * 8/1945 Mattox ................ C07C 1/213
                                                  585/606
(Continued)

FOREIGN PATENT DOCUMENTS

FR       1329340 A      6/1963
FR       3032707 A1     8/2016
(Continued)

OTHER PUBLICATIONS

International Search Report dated Dec. 4, 2017 issued in corresponding PCT/EP2017/076057 Application (3 pages).
English Abstract of JP 2012-072086 A published Apr. 12, 2012.

*Primary Examiner* — Ali Z Fadhel
(74) *Attorney, Agent, or Firm* — Millen, White, Zelano and Branigan, P.C.

(57) ABSTRACT

The invention relates to a method for producing butadiene that is fed with a butanediol feedstock, with said method comprising at least:
a) An esterification step comprising:
   A reaction section;
   A separation section producing a butanediol diester effluent, a water effluent, and a carboxylic acid effluent;
(Continued)

b) An esterification pyrolysis step;

c) A separation step comprising at least:

A cooling section producing a liquid pyrolysis effluent and a vapor pyrolysis effluent;

A gas-liquid washing section that is fed at the top with a fraction of the carboxylic acid effluent that is obtained from the separation section of step a) and at the bottom with said vapor pyrolysis effluent and producing at the top a butadiene effluent and at the bottom a washing effluent;

in which a carboxylic-acid-rich stream comprising at least a portion of the liquid pyrolysis effluent is recycled to step a);

d) A separation step.

15 Claims, 2 Drawing Sheets

(51) Int. Cl.
    *C07C 7/00*     (2006.01)
    *C07C 7/06*     (2006.01)

(56) References Cited

U.S. PATENT DOCUMENTS

| | | |
|---|---|---|
| 4,595,788 A | 6/1986 | Yamamoto et al. |
| 2018/0022682 A1 | 1/2018 | Richard et al. |

FOREIGN PATENT DOCUMENTS

| | | |
|---|---|---|
| GB | 946968 A | 1/1964 |
| JP | 2012-72086 A | 4/2012 |

\* cited by examiner

METHOD FOR PRODUCING AND PURIFYING 1,3-BUTADIENE

TECHNICAL FIELD OF THE INVENTION

The invention relates to the production of 1,3-butadiene from butanediol.

PRIOR ART

Today, 95% of the production of 1,3-butadiene is ensured by the steam-cracking of hydrocarbons and the subsequent extraction of diolefins within a $C_4$ distillation fraction by extractive distillation methods.

The change in costs of raw materials leads to operating the steam-cracking units with feedstocks that are increasingly light because they are less costly, bringing about the reduction in production of the $C_4$ fraction and consequently of 1,3-butadiene. Alternating methods for producing 1,3-butadiene should therefore be found.

A method for producing 1,3-butadiene from 2,3-butanediol, carried out on a pilot scale in 1945 in the USA, is described in the patents FR 859902, U.S. Pat. Nos. 2,383,205, 2,372,221, and in *Industrial & Engineering Chemistry*, 37 (9), 1945, pp. 865 to 908. This method consists of two primary steps:

The esterification of 2,3-butanediol by a carboxylic acid to form the corresponding diester;

The pyrolysis of diester for producing 1,3-butadiene and carboxylic acid, with the latter being recycled in the esterification step.

This method was developed because the direct dehydration of 2,3-butanediol leads to the very large majority formation of methyl ethyl ketone (MEK), which cannot be dehydrated into 1,3-butadiene. This method is particularly advantageous because the step for pyrolysis of 2,3-butanediol diester can be carried out with very good yields (typically more than 80 mol %), and the 1,3-butadiene that is obtained is of a high level of purity (typically approximately 99% by weight).

Nevertheless, the purity of the butadiene that is thus obtained, although of a high level, is still not adequate to meet the current specifications. However, this very high level of purity is crucial for the use of the 1,3-butadiene in various applications (fine chemistry, elastomer).

This invention makes it possible to eliminate this problem of the prior art. Actually, the applicant has discovered a concatenation of individual operations that makes it possible to eliminate the several impurities that are contained in the stream of 1,3-butadiene, making it possible to upgrade the 1,3-butadiene that is produced from a high level of purity to a very high level of purity (i.e., to current specifications), while ensuring its very good butadiene extraction yields (very little loss).

Object and Advantage of the Invention

The invention relates to a method for producing butadiene from butanediol that is fed with a butanediol feedstock, with said method comprising at least:

a) An esterification step comprising:
   A reaction section that is fed with at least said butanediol feedstock, a carboxylic-acid-rich stream that is obtained from step c), and at least one fraction of the carboxylic acid effluent that is obtained from the separation section of step a);
   A separation section that separates the effluent that is obtained from the reaction section into at least one butanediol diester effluent, a water effluent, and a carboxylic acid effluent;
   with said reaction section being implemented in the presence of an acid catalyst, at a pressure of between 0.01 and 1.0 MPa, and at an MMH in the reaction section (molar flow rate of diol feeding said section with a catalyst mol number in said section) of between 0.05 and 25 $h^{-1}$;

b) A pyrolysis step comprising a pyrolysis reactor that is fed with at least said butanediol diester effluent that is obtained from the esterification step a), carried out at a temperature of between 400 and 650° C. in such a way as to produce a pyrolysis effluent;

c) A step for separation of said pyrolysis effluent that is obtained from step b), comprising at least:
   A section for cooling said pyrolysis effluent to a temperature that is lower than 150° C., producing a liquid pyrolysis effluent and a vapor pyrolysis effluent;
   A gas-liquid washing section that is fed at the top with at least one fraction of the carboxylic acid effluent that is obtained from the separation section of step a) and at the bottom with said vapor pyrolysis effluent and producing a butadiene effluent at the top and a washing effluent at the bottom;
   in which a carboxylic-acid-rich stream comprising at least a portion of the liquid pyrolysis effluent is recycled to step a).

d) A purification step that is fed with the butadiene effluent that is obtained from step c) so as to bring the butadiene to the required specifications for its subsequent use.

One advantage of the invention is to produce high-purity 1,3-butadiene with a good yield, without drastically increasing the operating and investment costs. Another advantage of the invention is that the individual purification operations that are implemented generate effluents that can easily be recycled to other individual operations of the method, thus limiting the production of waste by the method in its entirety.

DETAILED DESCRIPTION OF THE INVENTION

Feedstock

In accordance with the invention, the method is fed with a butanediol feedstock comprising at least 90% by weight of butanediol. Butanediol is defined as all of the butanediol isomers, by themselves or in a mixture. In a preferred manner, the feedstock consists of more than 90% by weight of a butanediol that is selected from the group that consists of 2,3-butanediol, 1,4-butanediol, and the mixture thereof. Said butanediol feedstock can also comprise water.

Step a) for Esterification of Butanediol

The conversion method according to the invention comprises an esterification step a) comprising A reaction section that is fed with at least said butanediol feedstock, a carboxylic-acid-rich stream that is obtained from step c), and at least one fraction of the carboxylic acid effluent that is obtained from the separation section of step a);

A separation section separating the effluent that is obtained from the reaction section into at least one butanediol diester effluent, a water effluent, and a carboxylic acid effluent;

with said reaction section being implemented in the presence of an acid catalyst, at a pressure of between 0.01 and 1.0 MPa, and with an MMH in the reaction section (molar flow rate of diol feeding said section with a catalyst mol number in said section) of between 0.05 and 25 h$^{-1}$.

In a preferred manner, the carboxylic acid that is used is selected from the group that consists of formic acid, acetic acid, propanoic acid, butanoic acid, and benzoic acid. In a very preferred manner, the carboxylic acid that is used is acetic acid.

An addition of carboxylic acid from a source that is external to the method can advantageously be fed in a mixture with the carboxylic-acid-rich stream that is obtained from step c) and/or the fraction of the carboxylic acid effluent that is obtained from the separation section of step a) so as to compensate for the losses in carboxylic acid in the various sections of the method according to the invention.

Said reaction section can be produced by any method that is well known to one skilled in the art. It is implemented in the presence of an acid catalyst, which can be homogeneous or heterogeneous. The MMH in the reaction section (the molar flow rate of diol feeding said section with the catalyst mol number in said section) is between 0.05 and 25 h$^{-1}$, preferably between 0.15 and 20 h$^{-1}$. It is carried out at a pressure of between 0.01 and 1.0 MPa, in a preferred manner between 0.05 and 0.2 MPa, and in a very preferred manner between 0.08 and 0.12 MPa.

The ratio of the molar flow rates of butanediol and carboxylic acid at the inlet of said reaction section is advantageously between 2 and 6, in a preferred manner between 2 and 4, and in a very preferred manner between 2 and 3.5. The calculation of this ratio takes into account all of the streams feeding said reaction section.

In a preferred manner, the reaction section of the esterification step comprises a reactive distillation column, in which the butanediol feedstock is introduced into the upper part of the column, and the carboxylic acid is introduced into the lower part of the column.

Said reactive distillation column produces—at the top—a distillate that consists primarily of water produced by the esterification reaction and carboxylic acid introduced in excess and—at the bottom—a residue that consists primarily of butanediol diester and optionally carboxylic acid. This conversion step is such that the conversion of butanediol into butanediol diester is greater than 95 mol %, preferably greater than 99 mol %. The catalysts that are used for catalyzing the esterification reaction can also catalyze secondary reactions, which generate by-products for dehydration of the butanediol feedstock, which are drawn off into the distillate of said reactive distillation column.

In the preferred arrangement where the esterification step comprises a reactive distillation column, if the acid catalyst is homogeneous, it is introduced into the upper part of the column with the butanediol feedstock. If the catalyst is heterogeneous, it is kept in the reactive distillation column using a device that is well known to one skilled in the art.

The temperature within the distillation column is encompassed between the boiling point of the water that is produced at the top and that of the butanediol diester that is produced at the bottom. In the case where the carboxylic acid that is used is acetic acid, the temperature between the top and the bottom of the distillation column typically varies between 100 and 230° C.

Said esterification step a) comprises a separation section treating the effluent of the reaction section, advantageously the distillate of said reactive distillation column, with the latter consisting primarily of water that is produced by the reaction of esterification and carboxylic acid that is introduced in excess, but also dehydration by-products of the butanediol feedstock. Said separation section makes it possible to produce at least one water effluent that is eliminated from the method, and a carboxylic acid effluent that can be recycled to the reaction section. In an optional manner, this separation section also produces an effluent that primarily contains the by-products. These by-products comprise the dehydration by-products that are obtained from step a) as well as, optionally, the impurities that are produced in the pyrolysis step b) and recycled via the carboxylic-acid-rich stream.

These separations can be carried out by any method that is well known to one skilled in the art.

In a preferred manner, in the case where the acetic acid is used to carry out the esterification of butanediol, this separation is carried out by heterogeneous azeotropic distillation, by using a driver. In a non-limiting way, this driver can be isopropyl acetate, diethyl ether, or else ethyl tert-butyl ether.

Step b) for Pyrolysis of Butanediol Diester

The conversion method according to the invention comprises a pyrolysis step comprising a pyrolysis reactor that is fed with at least said butanediol diester effluent that is obtained from the esterification step a), carried out at a temperature of between 400 and 650° C. in such a way as to produce a pyrolysis effluent. The pyrolysis reaction can be implemented with or without the presence of a catalyst.

The pyrolysis reaction primarily transforms 1 mol of butanediol diester into 1 mol of 1,3-butadiene and thus releases 2 mol of carboxylic acid. Primarily means that more than 70 mol % of butanediol diester is converted into 1,3-butadiene. Preferably, more than 80 mol % of butanediol diester is converted into 1,3-butadiene. Said pyrolysis reactor, also called pyrolysis furnace, is operated at a temperature of between 400 and 650° C., preferably between 500 and 650° C., advantageously between 550 and 600° C., and in a preferred manner between 575 and 585° C. The optimal contact time within the pyrolysis furnace is based on the partial pressure of butanediol diester that is injected into the pyrolysis furnace. It is typically 1 second for a partial pressure of butanediol diester of 0.1 MPa, and 7 seconds for a partial pressure of butanediol diester of 0.04 MPa.

A certain number of impurities are also generated, such as methyl vinyl carbinol acetate (MVCA), methyl ethyl ketone enol acetate (MEKEA), and crotyl acetate (CA), and by-products such as vinylcyclohexene, methyl ethyl ketone (MEK), or methyl acetyl acetone (MAA).

Step c) for Separation

The separation step c) is fed with said pyrolysis effluent that is obtained from step b) and comprises at least:

A section for cooling said pyrolysis effluent to a temperature that is lower than 150° C., producing a liquid pyrolysis effluent and a vapor pyrolysis effluent;

A gas-liquid washing section that is fed at the top with a fraction of the carboxylic acid effluent that is obtained from the separation section of step a) and at the bottom with said vapor pyrolysis effluent and producing a butadiene effluent at the top and a washing effluent at the bottom.

A carboxylic-acid-rich stream comprising at least a portion of the liquid pyrolysis effluent is recycled to step a).

The pyrolysis effluent is cooled quickly to a temperature that is lower than 150° C., preferably lower than 50° C., in such a way as to limit the formation of degradation products by, for example, Diels-Alder reaction of 1,3-butadiene on itself to form vinylcyclohexene (VCH). This cooling section advantageously implements quenching. Quenching is defined as putting the pyrolysis effluent into contact with a sprayed cold liquid, called a quenching liquid. The gaseous effluent that is obtained from this contact constitutes the vapor pyrolysis effluent while the liquid effluent that is obtained from this contact constitutes the liquid pyrolysis effluent.

Advantageously, said quenching liquid is at least one fraction of said liquid pyrolysis effluent, cooled in advance before being reintroduced into the cooling section. In a preferred manner, this fraction of said liquid pyrolysis effluent is cooled to below 50° C., in a preferred manner below 40° C.

In a variant of the invention, said cooling section is implemented in a quenching tower in which a first quenching liquid, comprising at least one fraction of said liquid pyrolysis effluent that is cooled in advance, is introduced at an intermediate position within the quenching tower. A second quenching liquid, consisting of at least one fraction of the washing effluent that is obtained from the washing section, is introduced at a position that is located above, along a vertical axis, of said first quenching liquid.

In a preferred manner, the two quenching liquids are cooled to below 50° C., in a preferred manner below 40° C.

Said vapor pyrolysis effluent comprises more than 80% by weight, preferably more than 90% by weight, of 1,3-butadiene (without considering the optional inert diluent used to lower the partial pressure of butanediol diester within the pyrolysis furnace). Said vapor pyrolysis effluent can also contain light organic compounds that are generated in the pyrolysis step or during the cooling of the effluent.

Said vapor pyrolysis effluent feeds at the bottom the gas-liquid washing section, advantageously a gas-liquid washing column, which is fed at the top with a carboxylic acid effluent fraction that is produced within the separation section of step a). Washing with a carboxylic-acid effluent makes it possible to cut down on the impurities with surprising efficiency, while using a stream that is internal to the method. The use of a stream that is internal to the method also makes it possible to reduce the losses, where the recycling of the washing effluents prevents the purging of the compounds of value, such as butadiene. Said gas-liquid washing column produces at the top a butadiene effluent that feeds the purification step d) and at the bottom a washing effluent. The carboxylic-acid-rich stream that is recycled to step a) advantageously comprises, in addition to at least a portion of the liquid pyrolysis effluent, at least one fraction of said washing effluent. A fraction of this washing effluent, which can contain butadiene, advantageously feeds the cooling section of said step c) as a quenching liquid.

Advantageously, said vapor pyrolysis effluent can be compressed and/or cooled before being introduced into said gas-liquid washing section so as to improve the efficiency of the gas-liquid washing.

Said liquid pyrolysis effluent that is obtained from the cooling section of step c) for the most part consists of carboxylic acid. The most part is defined as at least 50% by weight, and preferably at least 70% by weight. It can also comprise other organic compounds, such as, for example, unconverted butanediol diester, intermediate pyrolysis compounds (i.e., butanediol diester molecules that have lost one carboxylic acid fragment of the two that are required for 1,3-butadiene to form), and optional by-products.

In an embodiment of the invention, the carboxylic-acid-rich stream comprises the liquid pyrolysis effluent that is not purified, i.e., without any intermediate purification, taking into account its high level of purity of carboxylic acid.

In another embodiment of the invention, the carboxylic-acid-rich stream comprises at least one fraction of the purified liquid pyrolysis effluent. That is, this fraction undergoes at least one purification step, with a fraction of the by-products generated in the pyrolysis step thus being able to be eliminated. This purification can be carried out by any techniques that are known to one skilled in the art. It is possible to cite in a non-limiting manner the distillation, the distillation with pressure change, the heterogeneous azeotropic distillation with the addition of a driver, or else the adsorption on a solid. The technique that is implemented greatly depends on the butanediol feedstock that is used. Actually, the liquid by-products that are generated in the pyrolysis step are greatly dependent upon the butanediol diester isomer that is fed into the pyrolysis step.

In this embodiment, a fraction of the purified liquid pyrolysis effluent is advantageously used to feed the cooling section as a quenching liquid, as discussed above. This implementation makes it possible to reduce the impurity content within the cooling section and thus to obtain a vapor pyrolysis effluent of a higher level of purity.

Step d) for Purification

The method according to the invention comprises a purification step d) that is fed with the butadiene effluent that is obtained from step c) so as to bring the butadiene to the specifications that are required for its subsequent use. These specifications depend on the use that is envisioned and are known to one skilled in the art.

Said purification step comprises at least:

A gas-liquid washing section that is fed at the top with a water-rich effluent and at the bottom with the butadiene effluent that is obtained from step c) and that produces a hydrated butadiene effluent and at the bottom an aqueous washing effluent;

A final purification section of the hydrated butadiene effluent making it possible to eliminate the water, the butenes, and the lighter products (for example hydrogen, methane, ethane, . . . ).

The separation step c) according to the invention makes it possible to obtain a butadiene effluent that is particularly simple to purify because of the reduction of impurities in the gas-liquid washing section with a surprising efficiency. Thus, the purification of the butadiene effluent can be done with the technologies that are known to one skilled in the art for bringing the butadiene to the specifications that are required for its subsequent use.

Said butadiene effluent that is obtained from step c) is very rich in 1,3-butadiene (i.e., more than 90% by weight) but can contain gaseous by-products that are generated in the pyrolysis step (carbon dioxide, carbon monoxide, hydrogen, methane, ethane, . . . ) and carboxylic acid.

Said water-rich effluent feeding said gas-liquid washing section can come from the separation section of step a) but is preferably a water stream that is external to the method.

Said aqueous washing effluent that is obtained from said gas-liquid washing section of step d) can advantageously be recycled to said separation section of step a), so as to limit the losses of carboxylic acid within the method, or else be eliminated from the method.

Said butadiene effluent that is obtained from step c) can advantageously be compressed and/or cooled before being introduced into said gas-liquid washing section of step d), so as to improve the efficiency of the washing.

Said final purification section of step d) can be implemented by:

The concatenation of a drying section, a cryogenic distillation, and a separation of the liquid/liquid extraction type, with implementation of a solvent;

A drying section followed by an extractive distillation step (optionally with intermediate cryogenic distillation);

An extractive distillation in the case where the solvent that is used tolerates the presence of water (optionally with intermediate cryogenic distillation).

The drying section can be produced by any means that is known to one skilled in the art. In a non-limiting manner, the hydrated butadiene effluent can be dried by azeotropic distillation or else by passing over an adsorbent. The drying section produces an aqueous effluent that is eliminated from the method and a dry butadiene effluent.

Said cryogenic distillation section produces at the top an incondensable gas effluent, primarily comprising the following compounds: carbon dioxide, carbon monoxide, hydrogen, methane, ethane, propylene . . . ) and at the bottom a purified butadiene effluent.

Said separation of the liquid/liquid extraction type is fed with the purified butadiene effluent that is obtained from the cryogenic distillation in an intermediate zone of a first liquid-liquid extraction column, into which a stream of polar solvent, preferably DMSO, is fed at the top. A saturated hydrocarbon solvent, preferably pentane or cyclohexane, is fed at the bottom.

The flow rates as well as the ratio of the flow rates of polar solvent to hydrocarbon solvent are regulated in such a way that the bulk of the butenes will be entrained by the hydrocarbon solvent, and the bulk of the butadiene will be entrained by the polar solvent.

The butenes/hydrocarbon mixture that is obtained at the top of the first extraction column is then treated in a first distillation column so as to obtain at the top a butene effluent and at the bottom the hydrocarbon solvent that can be recycled.

The butadiene/polar solvent mixture then feeds the top of a second liquid/liquid extraction column in which the butadiene is extracted from the polar solvent by direct contact with a larger quantity of hydrocarbon solvent than in the first liquid-liquid extraction column, which is introduced at the bottom of said second liquid-liquid extraction column.

The butadiene/hydrocarbon mixture that is obtained at the top of the second liquid-liquid extraction column is then treated in a second distillation column so as to obtain at the top a purified butadiene effluent and at the bottom the hydrocarbon solvent that can be recycled.

In a preferred manner, the liquid-liquid extraction columns are operated at a pressure of between 0.1 and 1 MPa and a temperature of between 20 and 60° C.

In a preferred configuration, said final purification section of step d) comprises an extractive distillation that is fed directly with said dry butadiene effluent, or hydrated if the solvent makes it possible, and that produces a gaseous effluent containing incondensable gases and $C_4$-type butene impurities, and a purified butadiene effluent. The extractive distillation can be carried out in a non-limiting manner with a polar solvent, miscible in the liquid phase with the mixture that is treated under the operating conditions of the method and non-volatile or not very volatile with respect to the treated products, advantageously with N-methyl-pyrrolidone, dimethylformamide, or acetonitrile.

The various sections for treatment and purification of butadiene that are implemented in said step d) can quite obviously also co-treat any stream comprising butadiene optionally produced by other methods similar to the method according to the invention.

Figure 1:
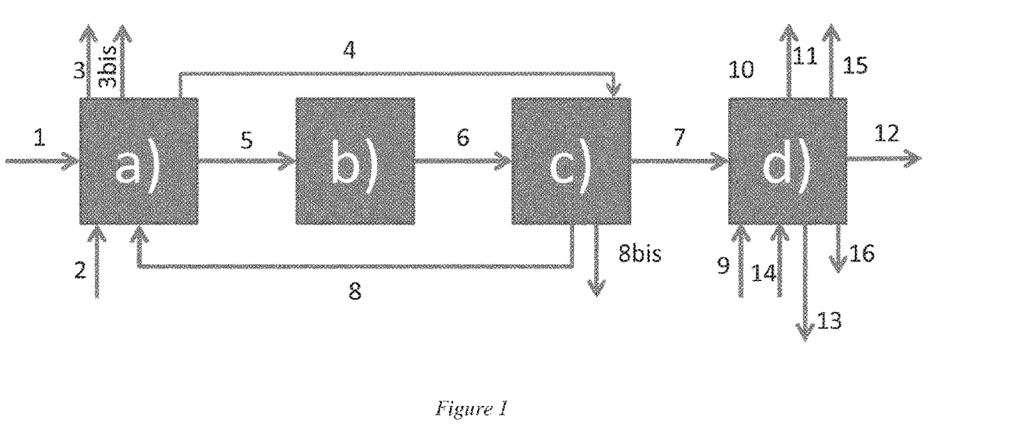
FIG. 1 presents a diagrammatic view of an arrangement of the method according to the invention.

In FIG. 1, the butanediol feedstock (1) undergoes a first esterification step a) with a carboxylic-acid-rich stream (8) and an addition of carboxylic acid (2) for producing, on the one hand, a butanediol diester effluent (5), and, on the other hand, a water effluent (3) and a by-product effluent (3*bis*) that are eliminated from the method. A carboxylic acid effluent (4) that feeds the separation step c) is also produced.

The butanediol diester effluent (5) feeds a pyrolysis step b) that produces a pyrolysis effluent (6) that feeds a separation step c).

The separation step c) is fed with a fraction of the carboxylic acid effluent that is produced by the separation section of step a) and by the pyrolysis effluent that is obtained from step b). The residual fraction of the carboxylic acid effluent that is produced by the separation section of step a) feeds the reaction section of said step a) (not shown). The separation step c) produces a carboxylic-acid-rich effluent (8) that is recycled to the esterification step a), a butadiene effluent (7) that feeds a purification step d), and a by-product effluent (8*bis*) that is eliminated from the method.

The purification step d) is fed with a water-rich effluent (9), with the butadiene effluent (7) that is obtained from the separation step c), and optionally with an addition of solvent (14). Step d) produces an aqueous washing effluent (10) that is advantageously recycled to the separation section of step a), an aqueous effluent (13) that is eliminated from the method, an effluent of incondensable gases (11), a draw-off of solvent that is to be purified (15), and optionally an effluent of liquid impurities (16) that are eliminated from the method. Step d) thus produces a purified butadiene (12).

During the pyrolysis step b), a small fraction of carboxylic acid can be cracked. The cracking products are eliminated from step d) in the effluent of incondensable gases (11). The addition of carboxylic acid (2), optional and preferred, introduced in step a) compensates for the losses of carboxylic acid in step b).

Figure 2:
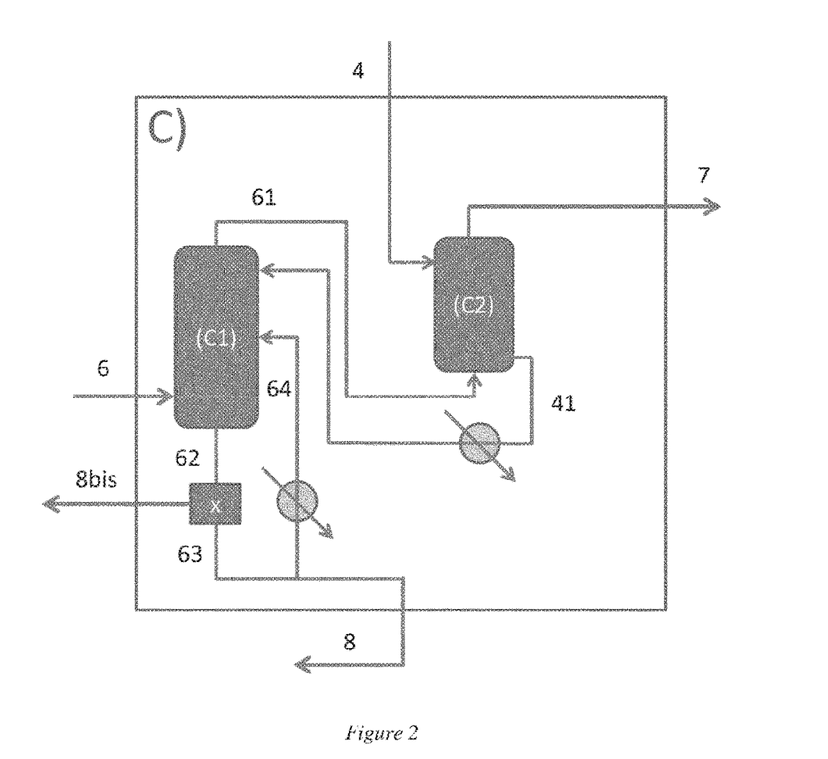
FIG. 2 has an arrangement of step c) according to the invention. The numbering is identical between FIGS. 1 and 2.

FIG. 2 has an arrangement of step c) according to the invention. The numbering is identical between FIGS. 1 and 2.

In FIG. 2, pyrolysis effluent (6) is introduced at the bottom of a quenching tower (C1). This quenching tower is fed with two separate quenching liquids, numbered (41) and (64). The feeding of the quenching liquid (41) is at a position that is higher than that of the quenching liquid (64). This quenching tower produces a vapor pyrolysis effluent (61) that feeds a gas-liquid washing column (C2) and a liquid pyrolysis effluent (62) that feeds an optional purification section (X). This purification section (X) produces a by-product effluent (8*bis*) that is eliminated from the method, and a purified liquid pyrolysis effluent (63), of which a fraction (64) is cooled before being recycled to the quenching tower (C1). The other fraction of the purified liquid pyrolysis effluent constitutes the carboxylic-acid-rich stream (8) that is recycled to step a) of the method.

The vapor pyrolysis effluent (61) is introduced at the bottom of the gas-liquid washing column (C2), which is fed at the top with a carboxylic acid effluent fraction (4) that is produced by the separation section of step a) of the method. Said gas-liquid washing column (C2) produces at the top a butadiene effluent (7) that feeds step d) for purification of butadiene and at the bottom a liquid effluent (41) that is cooled before being sent back to the top of the quenching tower (C1).

Figure 3:
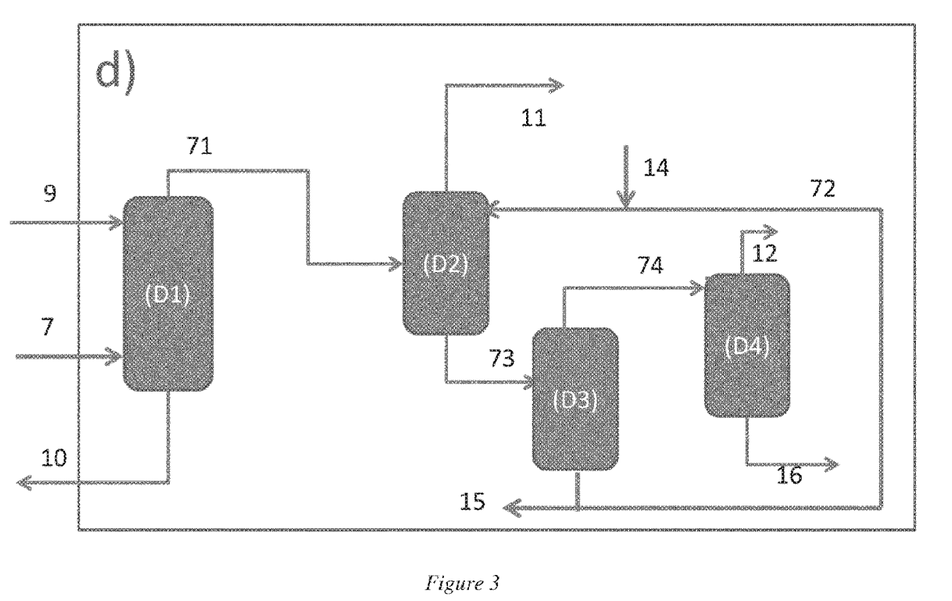
FIG. 3 has a particular arrangement of step d) according to a variant of the invention. The numbering is identical between FIGS. 1, 2, and 3.

FIG. 3 has a particular arrangement of step d) according to a variant of the invention. The numbering is identical between FIGS. 1, 2, and 3.

In FIG. 3, the butadiene effluent (7) that is obtained from step c) is introduced at the bottom of a gas-liquid washing column (D1), which is fed with a water-rich effluent (9) that is external to the method or that comes from the separation section a) (3). The gas-liquid washing column (D1) produces at the bottom an aqueous washing effluent (10) that is advantageously recycled to the separation section of step a) and a hydrated butadiene effluent (71) that feeds an extractive distillation section, composed of a first extractive distillation column (D2), also fed with recycled solvent (72) and an addition of solvent (14).

This column (D2) produces at the top an incondensable gas effluent (11) that is eliminated from the method and at the bottom a purified butadiene effluent (73). This effluent feeds a distillation column (D3) that makes it possible to recover at the bottom the solvent (72) that is recycled to the column (D2) and at the top the purified butadiene without solvent (74). A draw-off of solvent is possible via the stream (15). A last distillation column (D4) makes it possible to eliminate from the method the possible traces of heavy impurities by separating the purified butadiene without solvent (74) into a purified butadiene (12) with the required specifications drawn off at the top and an effluent (16) with heavy impurities drawn off at the bottom.

EXAMPLE

This example shows that the concatenation of the steps of esterification, pyrolysis, separation, and purification, with, on the one hand, the recycling of the liquid pyrolysis effluent to the esterification step and to the separation step of butadiene and, on the other hand, the recycling of the carboxylic acid effluent to the steps for purification of butadiene, leads to the production of 150 kt/year of 1,3-butadiene with more than 99.9% by weight of purity and with very small losses of reagents (operating period of 8,000 hours per year). There is thus synergy between the esterification/pyrolysis concatenation and the recycling of the liquid pyrolysis effluent and the concatenation of separation and purification steps fed with the pyrolysis effluent.

The following example is based on method simulations taking into account the recycling of streams and integrating thermodynamic data based on literature and data points (binary liquid-vapor balance data). In each of the examples, the feedstock flow rate is adjusted in such a way as to obtain an annual production of 150 kt/year of a butadiene having a purity of between 99.5 and 100% by weight (in adaptation with the current use of the product), with an annual operating period of the method of 8,000 hours.

The overall yield of the simulated method is 48.9% expressed in terms of one ton of butadiene per ton of 2,3-butanediol for a theoretical yield of the reaction of 60%. Its efficiency, or the ratio of the overall yield to the theoretical yield, is therefore 81.6%. The butadiene fraction at the outlet of the simulated method is 99.98% by weight of butadiene.

Step a) for Esterification

A butanediol feedstock that consists of 2,3-butanediol and an acetic-acid-rich stream (88.5% by weight) feed an esterification step by reactive distillation (molar ratio of 3) to produce a butanediol diester effluent comprising 2,3-butanediol diacetate and a carboxylic acid distillate. The acetic-acid-rich stream is obtained from, on the one hand, the separation step c) (recycling of the liquid pyrolysis effluent) and, on the other hand, the acetic acid/water separation column by heteroazeotropic distillation that makes it possible to eliminate the by-products that are formed by dehydration, the organic impurities, the water that is produced by the reaction, and the acetic acid.

This carboxylic acid distillate that is obtained from the reactive distillation contains 52.6% by weight of carboxylic acid, 30.4% by weight of water, and 16.9% of impurities. It feeds a distillation column comprising 25 theoretical stages and making it possible to eliminate at the top 100% of the impurities that are formed by dehydration. The residue from the column, consisting of 64.1% by weight of acetic acid and 35.9% by weight of water, feeds, with the aqueous washing effluent that is obtained from the gas-liquid washing column of section c), the acetic acid/water separation column by heteroazeotropic distillation with a heterogeneous driver.

The water stream exiting from this column is used in part for the gas-liquid washing of the butadiene effluent of section c). The acetic acid stream at the bottom is directed toward the acetic acid washing column and toward the reactive distillation section.

Step b) for Pyrolysis

The butanediol diester effluent that is obtained from the esterification step a) is preheated from 235° C. to 400° C. and then introduced into a pyrolysis furnace that operates at 595° C. and 0.11 MPa. The conversion rate of the diester is 99.4% with a selectivity of the butadiene in relation to the diester of 81.7 mol %.

Step c) for Separation

In a first step, the pyrolysis effluent undergoes cooling from 595° C. to 170° C. in a quenching column, with this fast cooling making it possible to prevent the polymerization of butadiene, and consequently to stop the pyrolysis reactions. At the end of this cooling, a vapor pyrolysis effluent and a liquid pyrolysis effluent are recovered. This cooling is carried out by quenching with a fraction of the liquid pyrolysis effluent that was cooled in advance to a temperature of 35° C.

The composition of the liquid pyrolysis effluent is indicated in Table 1.

TABLE 1

Composition by mass and molar composition of the liquid pyrolysis effluent.

|  | % by Mass | Mol % |
| --- | --- | --- |
| AA | 83.44% | 90.76% |
| MVCA | 6.73% | 3.85% |
| MEKEA | 2.03% | 1.16% |
| CA | 3.88% | 2.22% |
| MAA | 2.03% | 1.16% |

AA = acetic acid,
MVCA = methyl vinyl carbinol acetate,
MEKEA = methyl ethyl ketone enol acetate,
CA = crotyl acetate,
MAA = methyl acetyl acetone A fraction (approximately 66%) of the liquid pyrolysis effluent is used for the quenching of the pyrolysis effluent. The remaining reaction is sent to an adsorption column before being recycled to the esterification section as a carboxylic-acid-rich stream.

The top of the quenching column, called a vapor pyrolysis effluent and consisting primarily of butadiene (92.2% by weight), methane (1.8% by weight), CO2 (5% by weight), and several oxidized impurities, is compressed to 0.3 MPa, which makes it possible to increase the temperature of this stream to 53° C. This stream then feeds a washing column with acetic acid comprising 5 theoretical stages. The acetic acid that is used is obtained from the bottom of the water/acetic acid separation column by heteroazeotropic distillation. Its composition is therefore 99.99% by weight of acetic acid and 0.01% by weight of diester. This washing makes it possible to eliminate more than 97% of the organic compounds entrained in the vapor pyrolysis effluent, or 125 kg/h of impurities such as the pyrolysis intermediate compounds and by-products formed during the pyrolysis step. The bottom of the column contains butadiene (7.2% by weight), which is therefore recycled to the quenching column. The loss of 1,3-butadiene is insignificant in this separation step. A butadiene effluent is drawn off at the top of the column.

Step d) for Purification

The butadiene effluent that is obtained from the acetic acid washing column and that consists of 90.4% by weight of butadiene is washed with water in a gas-liquid water washing column comprising 10 theoretical stages, so as to eliminate the remaining 3% by weight of acetic acid. The water-rich effluent that is used for the washing comes from the step for separation by heteroazeotropic distillation of the acetic acid and water. The aqueous washing effluent that is drawn off at the bottom of the column, consisting primarily of acetic acid (43% by weight) and water (55% by weight), is recycled to the column for separation by acetic acid/water heteroazeotropic distillation so as to reduce the addition of acetic acid at the butanediol esterification section.

The top of the butadiene-rich column at 92.1% is dried on a sieve and purified by the extractive distillation methods in order to produce a butadiene fraction with a purity of 99.9%.

Assessment of Butadiene Losses

Exiting from the pyrolysis furnace, the series of separation steps implemented so as to purify the butadiene of the oxidized compounds and to recover the acetic acid for its recycling leads to a 99.98% butadiene recovery level. The butadiene losses are noted in the following streams and represent less than 1% of the final butadiene production:

| Exiting Streams | Loss of Butadiene (kg/h) |
| --- | --- |
| Bottom of gas-liquid water washing column (step d) | 8.62 |
| Purification by extractive distillation (step d) | 168.7 |
| TOTAL | 177.4 |

Assessment of Acetic Acid Losses

An addition of acetic acid is necessary for the esterification reaction because of acetic acid reaction losses. The loss of acetic acid (except for reaction losses) noted in the stream that eliminates the organic compounds such as MEK, CA, and MVCA remains insignificant (0.8 kg/h).

The acetic acid losses at the pyrolysis furnace come from parasitic reactions. The MEK is not an acetic acid loss since the MEKEA releases a second acetic acid in transforming into MEK. The acetic acid also transforms into CO2 and CH4 that are found at the top of the butadiene purification section by cryogenic distillation or extractive distillation. Overall, the acetic acid reaction loss is 5,355 kg/h.

The invention claimed is:

1. A method for producing butadiene from a butanediol feedstock, said method comprising:
    a) An esterification step comprising:
        feeding a reaction section said butanediol feedstock, a carboxylic-acid-rich stream that is obtained from step c), and at least one fraction of a carboxylic acid effluent that is obtained from a separation section of step a) said reaction section comprises an acid catalyst and is operated at a pressure of between 0.01 and 1.0 MPa, and at an MMH in the reaction section (molar flow rate of diol feeding said section with a catalyst mol number in said section) of between 0.05 and 25 $h^{-1}$ to produce a reaction section effluent comprising butanediol diester;
        separating in the separation section the reaction section effluent into at least one butanediol diester effluent, a water effluent, and the carboxylicacid effluent;
    b) A pyrolysis step comprising feeding a pyrolysis reactor with at least said butanediol diester effluent that is obtained from the esterification step a), said pyrolysis carried out at a temperature of between 400 and 650° C. to produce a pyrolysis effluent;
    c) A separating step for separation of said pyrolysis effluent that is obtained from step b), comprising at least:
        cooling said pyrolysis effluent in a cooling section to a temperature that is lower than 150° C. to produce a liquid pyrolysis effluent and a vapor pyrolysis effluent;
        feeding the top of a gas-liquid washing section with at least one fraction of the carboxylic acid effluent that is obtained from the separation section of step a) and at the bottom of the gas-liquid washing section with said vapor pyrolysis effluent to produce a butadiene effluent at the top and a washing effluent at the bottom;
        recycling at least a portion of the liquid pyrolysis effluent to step a) as the carboxylic-acid-rich stream;
    d) A purification step that is fed with the butadiene effluent that is obtained from step c) comprising at least:
        introducing a stream comprising water to the top of a second gas-liquid washing section and introducing at the bottom of the second gas-liquid washing section the butadiene effluent that is obtained from step c) and producing a hydrated butadiene effluent and at the bottom an aqueous washing effluent;
        eliminating water, butenes and light products comprised in the hydrated butadiene effluent in a final purification section to produce butadiene.

2. The method according to claim 1, in which said butanediol feedstock comprises at least 90% by weight of a butanediol that is selected from the group that consists of 2,3-butanediol, 1,4-butanediol, and mixture thereof.

3. The method according to claim 1, in which the carboxylic acid that is used is selected from the group that consists of formic acid, acetic acid, propanoic acid, butanoic acid, and benzoic acid.

4. The method according to claim 1, in which the ratio of the molar flow rates of butanediol and carboxylic acid at the inlet of said reaction section of said step a) is between 2 and 6.

5. The method according to claim 1, in which the carboxylic acid that is used is acetic acid.

6. The method according to claim 5, in which said separation section of said step a) comprises heterogeneous azeotropic distillation in the presence of a driver.

7. The method according claim 1, in which said cooling section of said step c) comprises quenching, with the quenching liquid being at least one fraction of said liquid pyrolysis effluent, cooled in advance.

8. The method according claim 1, in which said cooling section of said step c) comprises quenching, with the quenching liquid being at least one fraction of said washing effluent that is obtained from said washing section of said step c).

9. The method according to claim 7, in which said cooling section of said step c) is implemented in a quenching tower in which a first quenching liquid, comprising a fraction of said liquid pyrolysis effluent that is cooled in advance, is introduced at an intermediate position within the quenching tower, and a second quenching liquid, consisting of the washing effluent that is obtained from the washing section of said step c), is introduced at a position that is located above said first quenching liquid, along a vertical axis.

10. The method according to claim 1, in which said carboxylic-acid-rich stream that is recycled to step a) comprises, in addition to at least a portion of the liquid pyrolysis effluent, at least one fraction of said washing effluent that is obtained from the washing section of said step c).

11. The method according claim 1, in which the carboxylic-acid-rich stream comprises purified liquid pyrolysis effluent.

12. The method according to claim 7, in which a fraction of purified liquid pyrolysis effluent is used to feed the cooling section of said step c) as a quenching liquid.

13. The method according to claim 1, in which said carboxylic-acid-rich stream comprises non-purified liquid pyrolysis effluent from step c).

14. The method according to claim 1, in which an addition of carboxylic acid from a source that is external to the method is fed in a mixture with the carboxylic-acid-rich stream that is obtained from step c) and/or the fraction of the carboxylic acid effluent that is obtained from the separation section of step a).

15. The method according to claim 1, in which the stream comprising water that feeds the gas-liquid washing section of said step d) comprises the water effluent that is obtained from the separation section of said step a).

* * * * *